(12) United States Patent
Addis

(10) Patent No.: US 6,626,866 B1
(45) Date of Patent: Sep. 30, 2003

(54) CARDIOPLEGIA ACCESS VIEW PROBE AND METHOD OF USE

(75) Inventor: Bruce Addis, Redwood City, CA (US)

(73) Assignee: Edwards Lifesciences Corp., Irvine, CA (US)

(*) Notice: Subject to any disclaimer, the term of this patent is extended or adjusted under 35 U.S.C. 154(b) by 615 days.

(21) Appl. No.: 09/614,425

(22) Filed: Jul. 12, 2000

Related U.S. Application Data

(63) Continuation of application No. 09/145,809, filed on Sep. 2, 1998, now Pat. No. 6,099,498.

(51) Int. Cl.[7] .................... A61M 1/00; A61M 5/00; A61B 18/18; A61B 8/14
(52) U.S. Cl. ............... 604/118; 604/96.01; 604/248; 604/103.07; 600/459; 600/462; 606/16
(58) Field of Search ................. 604/507–9, 102, 604/96.01, 118, 119, 128, 129, 148, 164.11, 167.01–167.04, 190, 200–2, 205–6, 236–38, 264, 278, 523, 532, 536–39, 246–47, 540–44, 20, 167.05; 606/16, 15, 191–92, 194, 195; 600/466–67, 459, 462; 128/DIG. 3, 898

(56) References Cited

U.S. PATENT DOCUMENTS

| | | |
|---|---|---|
| 5,505,698 A | 4/1996 | Booth et al. |
| 5,700,243 A | 12/1997 | Narciso, Jr. |
| 5,820,600 A | 10/1998 | Carlson et al. |
| 5,833,682 A | 11/1998 | Amplatz et al. |
| 5,840,075 A | 11/1998 | Mueller et al. |
| 5,855,210 A | 1/1999 | Sterman et al. |
| 5,913,842 A | 6/1999 | Boyd et al. |
| 5,928,192 A | 7/1999 | Maahs |

*Primary Examiner*—Angela D. Sykes
*Assistant Examiner*—Patricia Bianco
(74) *Attorney, Agent, or Firm*—O'Melveny & Myers LLP

(57) ABSTRACT

A probe having the ability to deliver cardioplegia solution to the coronary sinus under direct visualization and to provide venous drainage from the right atrium for cardiopulmonary bypass. The probe has an elongate tubular member, including a distal end, a proximal end, and a lumen. A membrane, optionally perforated, mounted within the lumen of the tubular member partitions the lumen and is removable or penetrable by a cardioplegia catheter. The distal end comprises a toroidal balloon or a circumferential recessed vacuum manifold. A vacuum port communicates with the distal end of the tubular member or the vacuum manifold. Methods of using the cardioplegia access view probe for catheterization of the coronary sinus and for venous return as herein described are also disclosed.

11 Claims, 4 Drawing Sheets

CARDIOPLEGIA ACCESS VIEW PROBE AND METHOD OF USE

This is a continuation of U.S. application Ser. No. 09/145,809, filed Sep. 21, 1998, now U.S. Pat. No. 6,099,498, which is hereby expressly and fully incorporated herein by reference.

FIELD OF THE INVENTION

The present invention relates generally to a probe which facilitates delivery of cardioplegia in the coronary sinus and provides venous drainage for cardiopulmonary bypass, and more particularly to a probe which can be placed around the coronary sinus under direct visualization.

BACKGROUND OF THE INVENTION

Coronary artery disease remains the leading cause of morbidity and mortality in Western societies. Narrowing or blockage of the coronary arteries often results in myocardial ischemia and infarction. Different approaches have been developed for treating coronary artery disease, including balloon angioplasty, atherectomy, laser ablation, stents, and coronary artery bypass grafting surgery. Excellent long-term results have been achieved with conventional coronary bypass surgery. However, significant mortality and morbidity still exist due to the use of cardiopulmonary bypass for circulatory support and the traditional method of access by median sternotomy.

Minimally invasive concepts have been adopted in cardiac surgery to make coronary revascularization less invasive. In the port-access approach, a cardiac procedure is performed through minimal access incisions often made between a patient's intercostal space and cardiopulmonary support is instituted through an extra-thoracic approach.

In both conventional and minimally invasive coronary artery bypass grafting surgeries, and other cardiac surgeries such as heart valve repair or replacement, septal defect repair, pulmonary thrombectomy, atherectomy, aneurysm repair, aortic dissection repair and correction of congenital defects, cardiopulmonary bypass and cardiac arrest are often required. In order to arrest the heart, the heart and coronary arteries must be isolated from the peripheral vascular system, so that cardioplegia solution can be infused to paralyze the heart without paralyzing the peripheral organs. Cardiopulmonary bypass is then initiated to maintain peripheral circulation of oxygenated blood.

In conventional coronary artery bypass surgery, cardioplegia solution is usually administered through a catheter inserted into the aorta. Problems associated with this approach are that an additional wound site is generally required for administering cardioplegia, and that a cardioplegia catheter, located in the vicinity of the surgical field, may interfere with a surgeon's operation. Retrograde administration of cardioplegia to the coronary sinus as an alternative approach has been shown to be beneficial to the heart. In minimally invasive coronary artery bypass surgery, placement of a cardioplegia catheter often requires fluoroscopic guidance, and circulatory isolation of the heart and coronary blood vessels generally involves insertion of multiple large catheters in either the neck, or the groin, or both to remove blood from the superior vena cava and inferior vena cava for cardiopulmonary bypass. Problems with this procedure are that excess catheterization and use of fluoroscopy may be associated with increased morbidity.

New devices and methods are therefore desired for isolating the heart and coronary blood vessels from the peripheral vascular system and arresting cardiac function, particularly devices which do not require multiple cannulation sites, fluoroscopy, and/or additional cardioplegia catheter insertion.

SUMMARY OF THE INVENTION

The present invention provides a cardioplegia access view probe having the ability to deliver cardioplegia solution to the coronary sinus and drain venous blood for cardiopulmonary bypass. The probe further has the ability to provide direct visualization of the right atrium and coronary sinus for placement of a cardioplegia catheter. The cardioplegia access view probe comprises an elongate tubular member having a proximal end, a distal end, and a lumen therebetween. In a preferred embodiment, a toroidal balloon is attached to the distal end of the tubular member, which comprises a balloon inflation lumen.

The lumen of the tubular member is partitioned into a distal and a proximal segment by a membrane mounted within the lumen. The membrane can be removable or can be punctured by a cardioplegia catheter. A vacuum port in communication with the distal segment of the tubular member extends proximally and is operable from the proximal end of the probe. The tubular member may further include one or more drainage ports for draining venous blood from the right atrium. Deoxygenated blood may be delivered to a bypass-oxygenator machine through the proximal end of the tubular member, which is adapted for attachment to the bypass-oxygenator machine. The probe may also include a fiberoptic light source and a diffuser at its distal end to assist a surgeon in visualizing the right atrium and coronary sinus for placement of a cardioplegia catheter.

In an alternative embodiment, instead of having a toroidal balloon at the distal end of the tubular member and a vacuum port, the distal end of the tubular member has a recess vacuum manifold, which extends circumferentially around the distal end of the tubular member and communicates with a vacuum port. This design simplifies construction of the probe by eliminating the toroidal balloon and its inflation lumen and port.

The present invention also provides methods for administering cardioplegia to the coronary sinus of the heart. The methods employ a cardioplegia access view probe as described above. According to one method, the distal end of the probe is inserted into the right atrial chamber after an incision is made in the right atrium. The distal end of the probe is positioned around the coronary sinus with the assistance of a fiberoptic light source included in the probe. A vacuum is then applied to the vacuum port to remove fluid, blood, or air around the coronary sinus. In the embodiment which includes a toroidal balloon, the balloon is inflated to provide stabilization of the probe and a seal around the coronary sinus when vacuum is applied.

To insert a cardioplegia catheter into the coronary sinus, the membrane is removed from the tubular member by pulling an attachment or other mechanism at the proximal end of the tubular member. Alternatively, the membrane, which may include at least one perforation line, can be punctured by a cardioplegia catheter. Either method allows a surgeon to visualize the coronary sinus directly for positioning the cardioplegia catheter without the need for fluoroscopy.

After placement of the cardioplegia catheter, cardioplegia solution can be delivered to the coronary sinus. Vacuum is removed, and the toroidal balloon or vacuum manifold is lifted from the atrial tissue. Venous blood can then be drained through the lumen of the probe and venous drainage ports optionally included in the elongate tubular member to a bypass-oxygenator machine to provide circulatory isolation of the heart and coronary blood vessels from the peripheral vascular system.

It will be understood that there are many advantages to using a cardioplegia access view probe as disclosed herein. For example, the probe of the invention provides (1) direct visualization of the right atrium and coronary sinus, obviating the need for fluoroscopy, (2) venous drainage for cardiopulmonary bypass, obviating the need for multiple cannulation sites, (3) a light source to illuminate the right atrium to assist in placement of a coronary sinus catheter, (4) a vacuum/vent to clear the view between the window and heart structure, (5) a simple method for administering retrograde cardioplegia via the coronary sinus, and (6) devices adapted for minimally invasive procedures.

DETAILED DESCRIPTION

Figure 1:
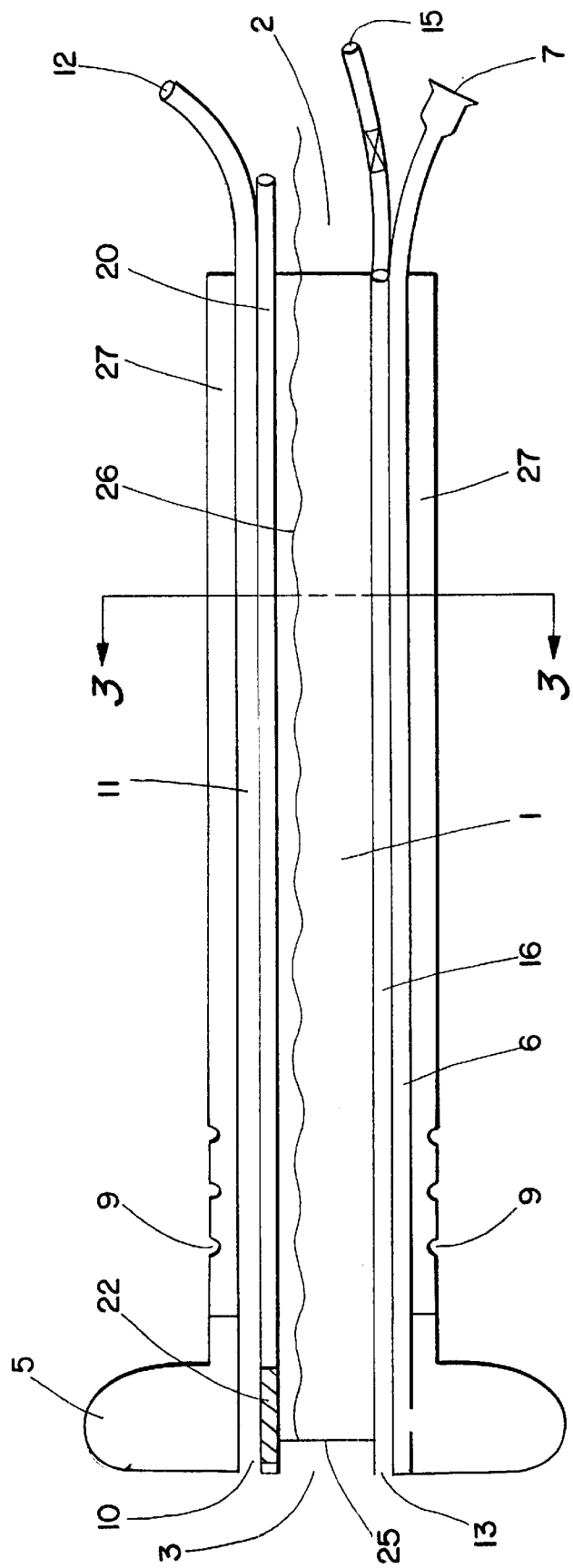
FIG. 1 depicts a cardioplegia access view probe according to one embodiment.

The devices and methods disclosed herein can be used to provide cardioplegia delivery for cardiac arrest and venous draining for cardiopulmonary bypass in cardiovascular surgeries, including coronary artery bypass grafting, heart valve repair, atherectomy, aneurysm repair, septal defect repair, pulmonary thrombectomy, aortic dissection repair, and correction of congenital defects. A preferred embodiment of a cardioplegia access view probe is depicted in FIG. 1. The probe has lumen 1, proximal end 2, and distal end 3. Toroidal balloon 5 is attached to the distal end and in communication with lumen 6 and inflation port 7. The probe also includes drainage ports 9 in communication with annular lumen 27 which may be used to deliver venous blood to a bypass-oxygenator machine through proximal end 2. Membrane 25 is positioned within lumen 1 and can be removed by pulling on attachment 26. The probe provides venous drainage to a bypass-oxygenator machine through lumen 1 when membrane 25 is removed. Fluid or blood can be aspirated through port 10 when vacuum is applied at vacuum inlet 12. Another vacuum port 13 located beneath membrane 25 communicates with lumen 16, which has vent 15 and one-way valve 14 to allow exchange of air or normal saline for displaced blood or fluid. A fiberoptic light source which has light diffuser 22 can be placed in lumen 20 to provide illumination of the coronary sinus for positioning a cardioplegia catheter.

Figure 2:
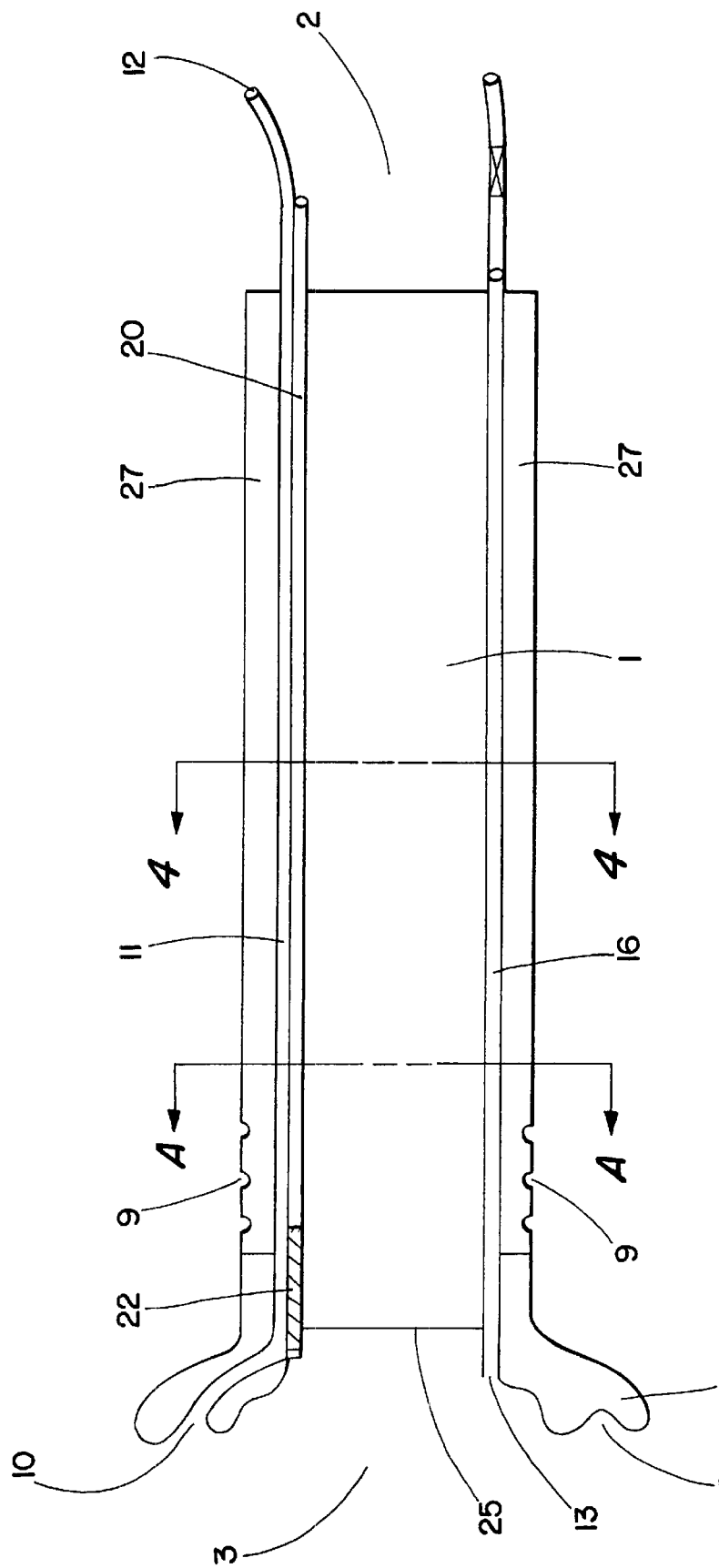
FIG. 2 depicts a cardioplegia access view probe according to another embodiment.
Figure 2A:
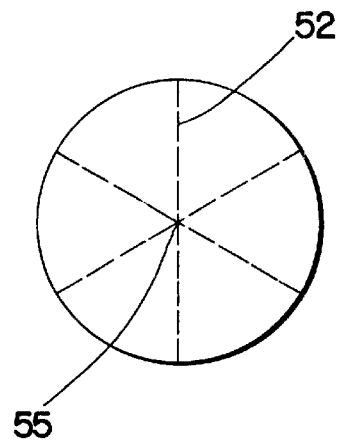
FIG. 2A depicts a cross-sectional view through section line A—A depicts the membrane in FIG. 2 having at least one perforation line.

FIG. 2 depicts an alternative embodiment of a cardioplegia access view probe. The probe has lumen 1, proximal end 2, and distal end 3. Manifold 30 has vacuum access 31 and the manifold extends circumferentially around the distal end of the probe. Vacuum port 10, located within the manifold, communicates with lumen 11 and inlet 12. When vacuum is applied at inlet 12, blood and fluid are removed from the distal end of the probe. Another vacuum port 13 located beneath membrane 25 communicates with lumen 16, which has vent 15 and one-way valve 14 to allow exchange of air or saline for displaced blood or fluid. A fiberoptic light source having light diffuser 22 can be placed in lumen 20 to illuminate the coronary sinus for positioning a cardioplegia catheter. Membrane 25, which may comprise at least one perforation line as shown in FIG. 2A, can be punctured by a cardioplegia catheter inserted into the lumen of the probe. In FIG. 2A, perforation lines 52 intersect at center 55 of the membrane. When a cardioplegia catheter is inserted through center 55, the membrane is torn along perforation lines 52, thereby leaving lumen 1 free to deliver venous blood from distal end 2 to proximal end 3 of the probe. Venous blood may also be drained from ports 9, which communicate with annular lumen 27, and is delivered to a bypass-oxygenator machine.

Figure 3:
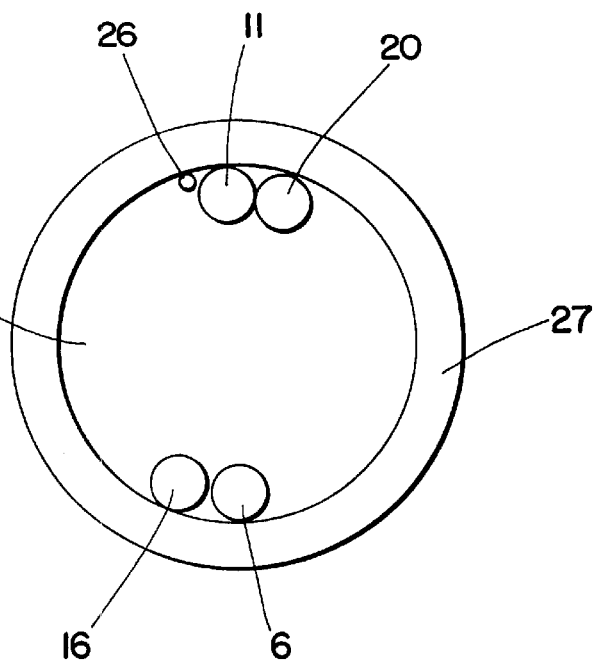
FIG. 3 depicts a cross-sectional view through section line 3—3 of the cardioplegia access view probe shown in FIG. 1.

FIG. 3 depicts a cross-sectional view through section line 3—3 of the probe depicted in FIG. 1. This embodiment has lumen 1 for inserting cardioplegia catheter and annular lumen 27 for delivering venous blood from the right atrium to a bypass oxygenator machine. Lumen 1 contains vacuum lumens 11 and 16, lumen 20 for fiberoptic light source, lumen 6 for inflating a toroidal balloon, and mechanism 26 which is attached to a membrane at the distal end of the probe.

Figure 4:
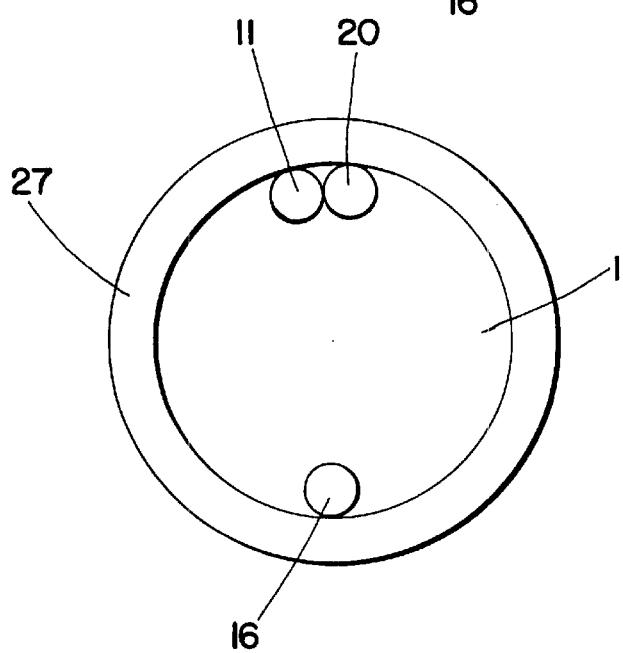
FIG. 4 depicts a cross-sectional view through section line 4—4 of the cardioplegia access view probe shown in FIG. 2.

FIG. 4 depicts a cross-sectional view through section line 4—4 of the probe depicted in FIG. 2. In this alternative embodiment, lumen 1 contains vacuum lumens 11 and 16, and lumen 20 for carrying a fiberoptic light source. This embodiment simplifies construction of the cardioplegia access view probe.

The length of a cardioplegia access view probe is generally between 3 and 15 inches, preferably approximately 7.5 inches. The outer diameter of the probe is generally between 0.3 and 1.5 inches, preferably approximately 0.75 inches. The inner diameter of the probe will generally be between 0.2 and 1.2 inches, preferably approximately 0.5 inches. The toroidal balloon, when expanded, will generally have a diameter between 0.5 and 3 inches, more preferably between 1 and 2 inches. The foregoing ranges are set forth solely for the purpose of illustrating typical device dimensions. The actual dimensions of a device constructed according to the principles of the present invention may obviously vary outside of the listed ranges without departing from those basic principles.

Figure 5:
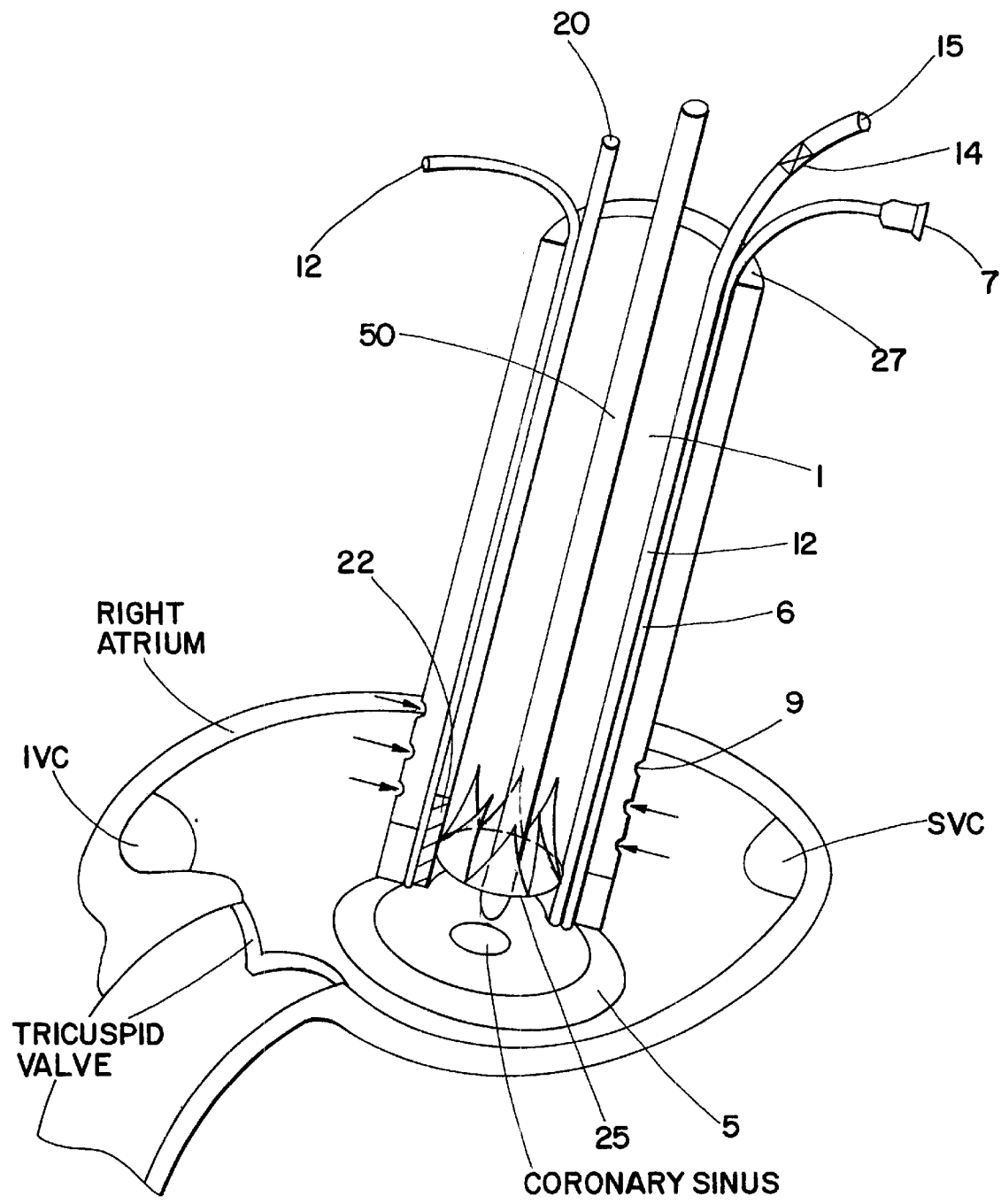
FIG. 5 depicts a cardioplegia access view probe containing a cardioplegia catheter positioned over a coronary sinus.

Methods for using the devices disclosed herein are illustrated in FIG. 5, which depicts a cardioplegia access view probe positioned over a coronary sinus. After an incision is made on a patient's right atrium, the distal end of the probe is inserted into the right atrium. In a minimally invasive coronary artery bypass surgery, the cardioplegia access view probe can be inserted percutaneously through an incision made in a patient's intercostal space. With the aide of a fiberoptic light source with diffuser 22 which focuses light distally toward the ostium of the coronary sinus, a surgeon can easily position the cardioplegia access view probe over the coronary sinus.

Toroidal balloon 5 is inflated through its connection with lumen 6 and port 7 to provide stabilization of the probe on the atrial tissue. When vacuum is applied on vacuum inlet 12, blood, fluid and air can be aspirated from the distal end of the probe, further facilitating a surgeon's visualization of the coronary sinus through membrane 25.

Once the surgeon has a clear view of the ostium of the coronary sinus, cardioplegia catheter 50 is inserted into lumen 1 and through membrane 25 to access the coronary sinus. Membrane 25, which may include at least one perforation line, is shown here separated into flaps, after the cardioplegia catheter is inserted through the membrane. To provide venous drainage through lumen 1, vacuum is removed from vacuum inlet 12, the probe is lifted away from the atrial tissue, and deoxygenated blood is carried from the distal end through lumen 1 of the probe to a bypass-oxygenator machine. Cardioplegia solution is then administered through cardioplegia catheter 50 into the coronary sinus. Venous blood in the right atrium may also be drained through venous drainage ports 9 and be delivered to a bypass-oxygenator machine through lumen 27. In this way, cardiac arrest and circulatory isolation of the heart and coronary blood vessels from the peripheral vascular system are achieved by the cardioplegia access view probe without he need for fluoroscopy, additional cannula, and multiple cannulation sites.

Although the foregoing invention has, for purpose of clarity of understanding, been described in some detail by way of illustration and example, it will be obvious that certain changes and modifications may be practiced which will still fall within the scope of the appended claim.

What is claimed is:

1. A cardioplegia access view probe, comprising:

an elongate tubular member having a proximal end, a distal end, and a lumen therebetween, the distal end having a recessed vacuum manifold extending circumferentially therearound;

a vacuum port communicating with the vacuum manifold; and a membrane mounted within the lumen of the tubular member and partitioning the lumen into a distal and a proximal segment.

2. The probe of claim 1, wherein the vacuum port is operable from the proximal end of the tubular member.

3. The probe of claim 1, wherein the vacuum port extends proximally.

4. The probe of claim 1, further comprising a venous drainage port.

5. The probe of claim 1, wherein the membrane is removable.

6. The probe of claim 1, wherein the membrane is adapted to be punctured by a cardioplegia catheter.

7. The probe of claim 1, further comprising a vacuum check valve.

8. The probe of claim 1, further comprising a fiberoptic light source.

9. The probe of claim 1, further comprising a light diffuser on the distal end of the tubular member.

10. The probe of claim 1, wherein the proximal end of the tubular member is adapted for attachment to a bypass oxygenator machine.

11. The probe of claim 1, wherein the membrane comprises at least one perforation line.

* * * * *